United States Patent [19]
Kubodera

[11] Patent Number: 5,874,598
[45] Date of Patent: *Feb. 23, 1999

[54] PROCESS FOR PRODUCING 1,2,3-TRIOXYSTEROID DERIVATIVES

[75] Inventor: Noboru Kubodera, Shizuoka, Japan

[73] Assignee: Chugai Seiyaku Kabushiki Kaisha, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 757,657

[22] PCT Filed: Nov. 29, 1993

[86] PCT No.: PCT/JP93/01732

§ 371 Date: May 12, 1995

§ 102(e) Date: May 12, 1995

[87] PCT Pub. No.: WO94/12522

PCT Pub. Date: Jun. 9, 1994

Related U.S. Application Data

[63] Continuation of Ser. No. 433,507, May 12, 1995, abandoned.

[30] Foreign Application Priority Data

Nov. 27, 1992 [JP] Japan .................... 4-354360

[51] Int. Cl.$^6$ .............. C07J 9/00; C07J 53/00; C07J 71/00
[52] U.S. Cl. ............ 552/541; 552/510; 540/50; 540/51; 540/60
[58] Field of Search .................. 552/510, 541; 540/50, 51, 60

[56] References Cited

U.S. PATENT DOCUMENTS

| | | | |
|---|---|---|---|
| 4,046,760 | 9/1977 | Jones et al. | 260/239.55 |
| 4,666,634 | 5/1987 | Miyamoto et al. | 260/397.2 |

FOREIGN PATENT DOCUMENTS

82/02893  9/1982  WIPO .

OTHER PUBLICATIONS

Weissenberg et al., "Cleavage of the epoxide ring in trans–epoxy–alcohols by sodium borohydride in methanol". J. Chem. Soc. Perkin I, (6) pp. 565–568, 1978.

Weissenberg et al., "Studies on epoxides–VI: Opening reactions of alpha–substituted epoxysteroids". Tetrahedron, vol. 29, p. 353–358, 1973.

Ochi et al., "Synthetic studies of vitamin D3 analogues from bile acids. Part 3 . . . ". J. Chem. Soc. Perkin I, vol. 1979(1), pp. 165–169, 1979.

Weissenberg, et al, J. Chem. Soc., Perkin Trans. I (6), pp. 565–568 (1978).

Weissenberg, et al, Tetrahedron, 29(2), pp. 353–358 (1973).

Ikekawa, Nobuo, 'Structures and Biological Acivities of Vitamin D Metabolites and their Analogs', Medicinal Research Reviews, vol. 7, No. 3, pp. 333–366, 1987.

*Primary Examiner*—José G. Dees
*Assistant Examiner*—Barbara Badio
*Attorney, Agent, or Firm*—Browdy and Neimark

[57] ABSTRACT

A process for the production of a compound of formula (II), which comprises reacting an epoxy compound of formula (I) with an alcohol, wherein the reaction is carried out under a basic condition.

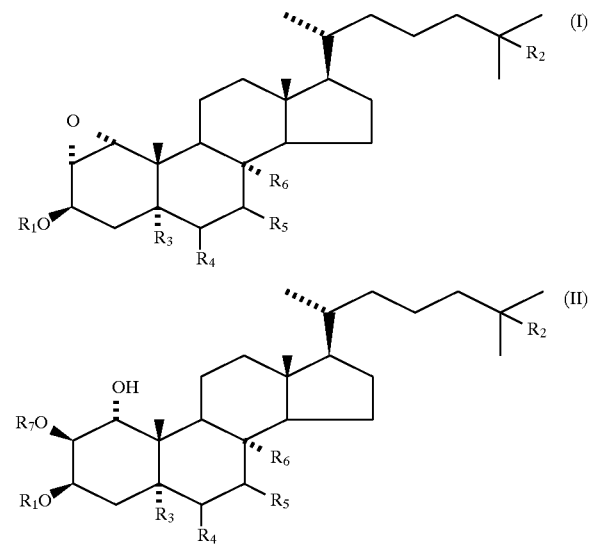

$R_1$, $R_2$, $R_3$, $R_4$, $R_5$, and $R_6$ are as defined in the specification. The compounds are useful intermediates for the production of vitamin $D_3$ derivatives.

19 Claims, No Drawings

PROCESS FOR PRODUCING 1,2,3-TRIOXYSTEROID DERIVATIVES

This application is a continuation, of application Ser. No. 08/433,507, filed May 12, 1995, now abandoned, which is a 371 of PCT/JP93/01732, filed Nov. 29, 1993.

TECHNICAL FIELD

The present invention relates to a process for synthesizing provitamin D compounds or provitamin D compounds in which the 5,7-diene structure is protected which are intermediates for synthesis of vitamin D derivatives having a substituent at the 2β-position which have various physiological activities such as a calcium controlling activity in vivo and a differentiation deriving activity of tumor cells, etc.

More specifically, the present invention relates to a process for introducing a substituent into the 2β-position by reacting a 1α,2α-epoxy compound with an alcohol under basic conditions.

1. Background Art

Hitherto, in introducing a substituted lower alkoxy group at the 2β-position of vitamin D derivatives, a process in which the addition reaction of an alcohol to 1α,2α-epoxy compound is carried out under an acidic conditions has been known (Japanese Patent Application (Kokai) No. 61-267549), but this process is not satisfactory due to its low yield, etc.

2. Disclosure of Invention

As a result of extensive studies, the present inventors found that, in introducing a substituent at the 2β-position by reacting a 1α,2α-epoxy compound (1) represented by the formula (I):

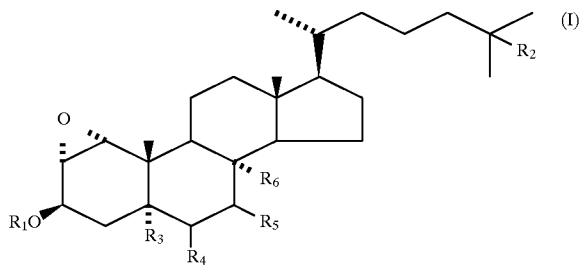

(wherein $R_1$ represents a hydrogen atom or a protective group, $R_2$ are such a hydrogen atom or a hydroxyl group, $R_3$, $R_4$, $R_5$ and $R_6$ are such that each of $R_3$ and $R_4$, and $R_5$ and $R_6$ forms a double bond, or $R_4$ and $R_5$ form a double bond, and $R_3$ and $R_6$ bond to dienophile which is capable of protecting a conjugated double bond), with an alcohol, the reaction proceeds even under basic conditions whereby a ring-cleaved product represented by the following formula (II) can be obtained in a high yield:

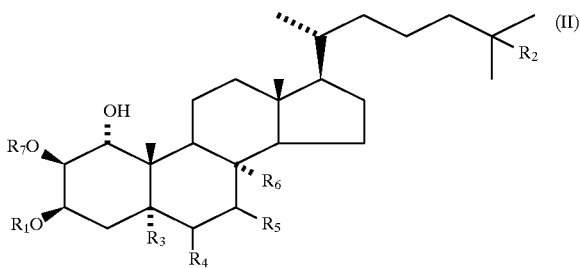

(wherein $R_1$ represents a hydrogen atom or a protective group, $R_2$ represents a hydrogen atom or a hydroxyl group, $R_3$, $R_4$, $R_5$ and $R_6$ are such that each of $R_3$ and $R_4$, and $R_5$ and $R_6$ forms a double bond, or $R_4$ and $R_5$ form a double bond, and $R_3$ and $R_6$ bond to dienophile which is capable of protecting a conjugated double bond, and $R_7$ represents a lower alkyl group, a cycloalkyl group or a lower hydroxyalkyl group wherein the hydroxyl group may be protected.)

In the above reaction, protection of some functional groups which has been considered necessary in a conventional ring-cleaving reaction under an acidic condition becomes unnecessary, but the reaction may be carried out while protected. Further, in the process of this invention, the ring-cleaved product can be obtained in a high yield as compared with the reaction under acidic conditions.

The provitamin $D_3$ derivatives prepared according to the process of this invention can be converted into the corresponding vitamin $D_3$ derivatives by subjecting the provitamin $D_3$ derivatives to conventional thermal isomerization after irradiation with U.V. light.

In the present invention, examples of the protective groups in the formula include an acyl group such as an acetyl group, a pivaloyl group, a methoxycarbonyl group, a benzyloxycarbonyl group and a p-toluenesulfonyl group, an alkyl group which may be substituted such as a methyl group and a methoxymethyl group, and a substituted silyl group such as a trimethylsilyl group, a triethylsilyl group and a t-butyldimethylsilyl group, and, preferably, a trimethylsilyl group, a triethylsilyl group and a t-butyldimethylsilyl group.

The alcohol compound means an aliphatic monohydric or polyhydric alcohol having from 1 to 7 carbon atoms, and some of the hydroxyl groups thereof other than any one hydroxyl group thereof may be protected. Examples of the alcohol compound include propanol, butanol, pentanol, hexanol, cyclopropanol, cyclobutanol, cyclopentanol, cyclohexanol, ethylene glycol, 1,3-propanediol, 1,4-butanediol, 1,5-pentanediol, etc.

The lower alkyl group means a straight chain or a branched alkyl group having from 1 to 6 carbon atoms, for example, a methyl group, an ethyl group, an n-propyl group, an i-propyl group, an n-butyl group, an s-butyl group, a t-butyl group, etc. The cycloalkyl group means a cycloalkyl group having from 3 to 8 carbon atoms, for example, a cyclopropyl group, a cyclobutyl group, a cyclopentyl group, a cyclohexyl group, a cycloheptyl group, a cyclooctyl group, etc. The lower hydroxyalkyl group means an alkyl group having from 1 to 7 carbon atoms wherein at least one hydrogen atom is substituted with a hydroxyl group, for example, a 2-hydroxyethyl group, a 3-hydroxypropyl group, a 4-hydroxybutyl group, etc., preferably a 3-hydroxypropyl group.

The ring cleaving reaction according to the present invention can be carried out in the presence or absence of a solvent, and, when the solvent is present, examples thereof include ether type solvents such as tetrahydrofuran and dioxane, and aromatic type solvents such as benzene and toluene. Preferably, the reaction is carried out with benzene or without any solvent.

The reaction temperature can be from 50° to 150° C. preferably from 80° to 120° C.

The compound represented by the formula (I):

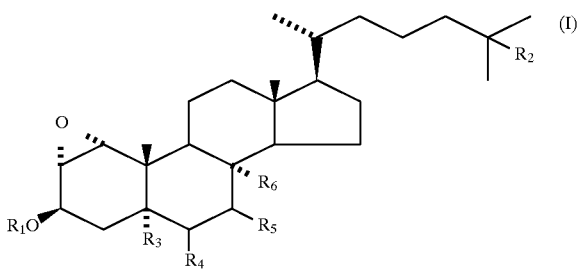

(wherein $R_1$ represents a hydrogen atom or a protective group, $R_2$ represents a hydrogen atom or a hydroxyl group, $R_3$, $R_4$, $R_5$ and $R_6$ are such that each of $R_3$ and $R_4$, and $R_5$ and $R_6$ forms a double bond, or $R_4$ and $R_5$ form a double bond, and $R_3$ and $R_6$ bond to dienophile which is capable of protecting a conjugated double bond) which can be used in the present invention, can be synthesized by the process described in, for example, Japanese Patent Application (Kokai) Nos. 50-84555 and 50-84560, and J. Org. Chem., 57, 5019–5020(1992).

The dienophile which is capable of protecting a conjugated double bond used in the present invention includes a compound represented by the formula (III):

(wherein A and B, which may be the same or different, each represents an alkoxy group having from 1 to 4 carbon atoms, or A and B, when taken together, represent a phenylimino group or an o-phenylene group, and Y represents a nitrogen atom or a methine (=CH—) group), and preferably, 4-phenyl-1,2,4-triazoline-3,5-dione, diethyl maleate, etc.

The basic condition means that a base is present in the reaction system.

The base which can be used in the present invention includes a metal base such as a metal alkoxide, a metal hydride and the like, for example, potassium t-butoxide and sodium hydride, preferably potassium t-butoxide. The base may be used alone or in combination with an additive such as a Crown ether, and examples of the combination with the additive include sodium hydride+15-Crown-5, potassium t-butoxide+18-Crown-6, potassium t-butoxide+dibenzo 18-Crown-6 and the like, and preferably, potassium t-butoxide+dibenzo 18-Crown-6.

The present invention is further illustrated by the following Examples and Reference Example in more detail.

REFERENCE EXAMPLE 1

Synthesis of 3β,25-dihydroxy-1α,2α-epoxy-5,7-cholestadiene

A solution of 49 mg ($8.3 \times 10^{-5}$ mol) of 1α,2α-epoxy-5α,8α-(3,5-dioxo-4-phenyl-1,2,4-triazolidino)-6-cholestene-3β,25-diol) in DMI (5 ml) was stirred in an argon atmosphere at 140° C. (bath temperature) for 5 hours. The reaction mixture was poured into water, and the resulting mixture was extracted twice with ethyl acetate, and then washed once with water. After drying the ethyl acetate layer over anhydrous magnesium sulfate, the solvent was distilled off under reduced pressure, and the resulting residue was purified by fractional thin layer chromatography (silica gel:ethyl acetate:n-hexane=55:45) to obtain 21 mg (62% yield) of the titled compound as a white powder.

Melting point: 173°–175° C. $^1$H-NMR(CDCl$_3$)δ: 0.64 (3H,s), 0.97(3H,d,J=6.3 Hz), 1.05(3H,s), 1.22(6H,s), 3.04 (1H,d,J=3.4 Hz), 3.33(1H,d,J=3.4 Hz), 3.90(1H,dd,J=10.7, 6.1 Hz), 5.36–5.42(1H,m), 5.70–5.72(1H,m) MS(m/z): 414 (M$^+$), 59(100%) UV λmax(nm): 290, 278, 268

EXAMPLE 1

Synthesis of 2β-(3-hydroxypropoxy)-1α,3β,25-trihydroxycholesta-5,7-diene

A mixture of 21 mg ($5.1 \times 10^{-5}$ mol) of 3β,25-dihydroxy-1α,2α-epoxy-5,7-cholestadiene, 294 μl ($4.1 \times 10^{-3}$ mol) of 1,3-propanediol, 19 mg ($1.5 \times 10^{-4}$ mol) of potassium t-butoxide and 4.8 mg ($1.3 \times 10^{-5}$ mol) of dibenzo-18-Crown-6 was stirred in an argon atmosphere at 110° C. (bath temperature) for 4 hours. The reaction mixture was poured into water, and the resulting mixture was extracted twice with ethyl acetate and washed once with a saturated aqueous sodium chloride solution. After drying the ethyl acetate layer over anhydrous magnesium sulfate, the solvent was distilled off under reduced pressure, and the resulting residue was purified by fractional thin layer chromatography (silica gel:dichloromethane:ethanol=100:15) to obtain 18 mg (72% yield) of the titled compound as a white powder.

Melting point: 118°–120° C. $^1$H-NMR(CDCl$_3$)δ: 0.62 (3H,s), 0.96(3H,d,J=6.3 Hz), 1.06(3H,s), 1.22(6H,s), 5.32–5.42(1H,m), 5.64–5.73(1H,m) MS(m/z): 490(M$^+$), 131 (100%) UV λmax(nm): 293, 281.5, 271, 262(shoulder)

EXAMPLE 2

Synthesis of 2β-(3-hydroxypropoxy)-1α,3β-dihydroxy-5,7-cholestadiene

A mixture of 275 mg ($6.9 \times 10^{-4}$ mol) of 1α,2α-epoxy-3β-hydroxy-5,7-cholestadiene, 4 ml ($5.5 \times 10^{-2}$ mol) of 1,3-propanediol, and 258 mg ($2.1 \times 10^{-3}$ mol) of potassium t-butoxide was stirred in an argon atmosphere at 110° C. (bath temperature) for 4.5 hours. The reaction mixture was poured into water, and the resulting mixture was extracted twice with diethyl ether and washed three times with water. Sodium chloride was added to the aqueous layer, and the mixture was extracted twice with ethyl acetate and washed once with a saturated aqueous sodium chloride solution. After drying the combined organic layer over anhydrous magnesium sulfate, the solvent was distilled off under reduced pressure, and the resulting residue was purified by flash column chromatography (silica gel:dichloromethane:ethanol=10:1) to obtain 229 mg (70% yield) of the titled compound as a white powder.

Melting point: 114°–116° C. $^1$H-NMR(CDCl$_3$)δ: 0.62 (3H,s), 0.87(6H,d,J=6.3 Hz), 0.94(3H,d,J=6.8 Hz), 5.32–5.39(1H,m), 5.63–5.73(1H,m) MS(m/z): 474(M$^+$), 380 (100%) UV λmax(nm): 293, 282, 271, 262(shoulder)

EXAMPLES 3 TO 8

The following compounds were synthesized in the same manner as described in Example 2 except for using various alcohols in place of 1,3-propanediol.

EXAMPLE 3

2β-Butoxy-1α,3β-dihydroxycholesta-5,7-diene $^1$H-NMR(CDCl$_3$)δ: 0.63(3H,s), 0.87(6H,d,J=6.6 Hz), 0.94(3H,d,J=6.9 Hz), 1.07(3H,s), 3.41–3.50(1H,m), 3.66–3.74(2H,m), 3.83–3.99(2H,m), 5.34–5.42(1H,m), 5.68–5.74(1H,m) MS(m/z): 472(M$^+$), 57(100%) UV λmax (nm): 293, 281, 270 IR(cm$^{-1}$): 3450, 2980, 2900, 1480, 1400, 1110, 1060, 750

EXAMPLE 4

2β-Cyclohexyloxy-1α,3β-dihydroxycholesta-5,7-diene $^1$H-NMR(CDCl$_3$)δ: 0.63(3H,s), 0.87(6H,d,J=6.6 Hz), 3.39–3.96(4H,m), 5.31–5.41(1H,m), 5.56–5.63(1H,m) MS(m/z): 498(M$^+$), 55(100%) UV λmax(nm): 290, 279, 269 IR(cm$^{-1}$): 3450, 2950, 2900, 1090,

EXAMPLE 5

2β-Cyclohexyloxy-1α,3β,25-trihydroxycholesta-5,7-diene $^1$H-NMR(CDCl$_3$)δ: 0.63(3H,s), 0.96(3H,d,J=6.3 Hz), 1.09(3H,s), 1.22(6H,s), 3.38–3.50(1H,m), 3.73–3.83(2H,m), 3.87–3.93(1H,m), 5.32–5.40(1H,m), 5.67–5.73(1H,m) MS(m/z): 514(M$^+$), 55(100%) UV λmax(nm): 293, 281, 271 IR(cm$^{-1}$): 3400, 2940, 2850, 1450, 1380, 990, 760

EXAMPLE 6

2β-(4-Hydroxybutoxy)-1α,3β,25-trihydroxycholesta-5,7-diene $^1$H-NMR(CDCl$_3$)δ: 0.63(3H,s), 0.96(3H,d,J=6.3 Hz), 1.06(3H,s), 1.22(6H,s), 3.41–4.00(7H,m), 5.33–5.40(1H,m), 5.68–5.73(1H,m) MS(m/z): 504(M$^+$), 55(100%) UV λmax (nm): 293, 281, 270 IR(cm$^{-1}$): 3420, 2950, 2900, 1480, 1390, 770

EXAMPLE 7

2β-Butoxy-1α,3β,25-trihydroxycholesta-5,7-diene $^1$H-NMR(CDCl$_3$)δ: 0.63(3H,s), 0.93(3H,t,J=7.3 Hz), 0.96 (3H,d,J=6.3 Hz), 1.07(3H,s), 1.21(6H,s), 3.40–3.52(1H,m), 3.66–3.77(2H,m), 3.84–4.00(2H,m), 5.33–5.41(1H,m), 5.67–5.74(1H,m) MS(m/z): 488(M$^+$), 59(100%) UV λmax (nm): 292, 281, 271 IR(cm$^{-1}$): 3450, 2950, 2900, 1490, 1390, 1100

EXAMPLE 8

2β-(5-Hydroxypentoxy)-1α,3β,25-trihydroxycholesta-5,7-diene $^1$H-NMR(CDCl$_3$)δ: 0.63(3H,s), 0.96(3H,d,J=6.3 Hz), 1.06(3H,s), 1.22(6H,s), 3.41–4.00(7H,m), 5.33–5.40(1H,m), 5.68–5.73(1H,m) MS(m/z): 518(M$^+$), 59(100%) UV λmax (nm): 293, 281, 270 IR(cm$^{-1}$): 3400, 2950, 2880, 1380, 1140, 970, 760

EXAMPLES 9 TO 14

The following vitamin D$_3$ derivatives were synthesized from the products of Examples 3 to 8 by thermal isomerization after irradiation of U.V. light under the conventional conditions.

EXAMPLE 9

2β-butoxy-1α,3β-dihydroxy-9,10-secocholesta-5,7,10(19)-triene $^1$H-NMR(CDCl$_3$)δ: 0.55(3H,s), 0.86(6H,d,J=6.6 Hz), 0.92(3H,d,J=6.0 Hz), 0.94(3H,t,J=7.4 Hz), 3.22(1H,dd,J= 9.1,2.8 Hz), 3.47–3.58(1H,m), 3.65–3.77(1H,m), 4.23(1H, brs), 4.29(1H,d,J=6.6 Hz), 5.08(1H,s), 5.49(1H,s), 6.06(1H, d,J=11.2 Hz), 6.36(1H,d,J=11.2 Hz) MS(m/z): 472(M$^+$), 109(100%) UV λmax(nm): 2.64, λmin(nm): 228 IR(cm$^{-1}$): 3400, 2950, 2860, 1460, 1380, 1100

EXAMPLE 10

2β-cyclohexyloxy-1α,3β-dihydroxy-9,10-secocholesta-5,7,10(19)-triene $^1$H-NMR(CDCl$_3$)δ: 0.55(3H,s), 0.86(6H,d,J=6.6 Hz), 0.92(3H,d,J=6.3 Hz), 3.35(1H,dd,J=9.4,2.5 Hz), 3.39–3.50 (1H,m), 4.12–4.18(1H,m), 4.19–4.30(1H,m), 5.07(1H,s), 5.49(1H,s), 6.06(1H,d,J=11.4 Hz), 6.36(1H,d,J=11.4 Hz) MS(m/z): 498(M$^+$), 56(100%) UV λmax(nm): 264, λmin (nm): 229

EXAMPLE 11

2β-cyclohexyloxy-1α,3β,25-trihydroxy-9,10-secocholesta-5,7,10(19)-triene $^1$H-NMR(CDCl$_3$)δ: 0.55(3H,s), 0.94(3H,d,J=6.3 Hz), 1.21(6H,s), 3.32–3.39(1H,m), 3.40–3.45(1H,m), 4.11–4.17 (1H,m), 4.22–4.29(1H,m), 5.07(1H,s), 5.49(1H,s), 6.06(1H, d,J=11.3 Hz), 6.34(1H,d,J=11.3 Hz) MS(m/z): 514(M$^+$), 55(100%) UV λmax(nm): 264, λmin(nm): 228

EXAMPLE 12

2β-(4-hydroxybutoxy)-1α,3β,25-trihydroxy-9,10-secocholesta-5,7,10(19)-triene $^1$-NMR(CDCl$_3$)δ: 0.55(3H,s), 0.59(3H,d,J=5.9 Hz), 1.21 (6H,s), 3.15–3.20(1H,m), 3.45–4.38(6H,m), 5.08(1H,s), 5.48(1H,s), 6.05(1H,d,J=11.6 Hz), 6.36(1H,d,J=11.6 Hz) MS(m/z): 504(M$^+$), 59(100%) UV λmax(nm): 263, λmin (nm): 229

EXAMPLE 13

2β-butoxy-1α,3β,25-trihydroxy-9,10-secocholesta-5,7,10(19)-triene $^1$H-NMR(CDCl$_3$)δ: 0.55(3H,s), 0.91–0.99(6H,m), 1.22 (6H,s), 3.18–3.26(1H,m), 3.47–3.77(2H,m), 4.23(1H,brs), 4.29(1H,d,J=6.6 Hz), 5.08(1H,s), 5.50(1H,s), 6.08(1H,d,J= 12.2 Hz), 6.34(1H,d,J=12.2 Hz) MS(m/z): 488(M$^+$), 59(100%) UV λmax(nm): 264, λmin(nm): 228

EXAMPLE 14

2β-(5-hydroxypentoxy)-1α,3β,25-trihydroxy-9,10-secocholesta-5,7,10(19)-triene $^1$H-NMR(CDCl$_3$)δ: 0.55(3H,s), 0.94(3H,d,J=6.6 Hz), 1.22(6H,s), 3.17–3.27(1H,m), 3.45–4.40 (6H,m), 5.08(1H, s), 5.50(1H,s) MS(m/z): 518(M$^+$), 69(100%) UV λmax(nm): 264, λmin(nm): 228 IR(cm$^{-1}$): 3400(br), 2930, 2860, 1460, 1380, 1100, 980, 740

I claim:

1. A process for producing a compound represented by the formula (II):

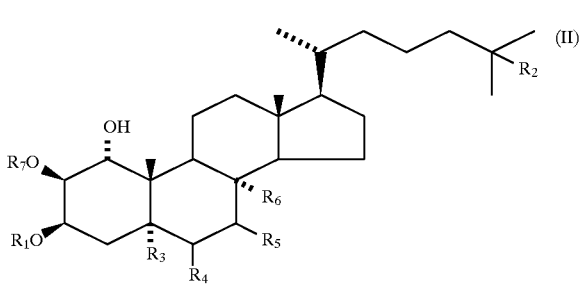

wherein $R_1$ represents a hydrogen atom or a protective group, $R_2$ represents a hydrogen atom or a hydroxyl group, $R_3$, $R_4$, $R_5$ and $R_6$ are such that each of $R_3$ and $R_4$, and $R_5$ and $R_6$ forms a double bond, or $R_4$ and $R_5$ form a double bond, and $R_3$ and $R_6$ bond to dienophile which is capable of protecting a conjugated double bond, and $R_7$ represents a lower alkyl group, a cycloalkyl group or a lower hydroxyalkyl group wherein the hydroxyl group may be protected, which comprises reacting an epoxy compound represented by the formula (I):

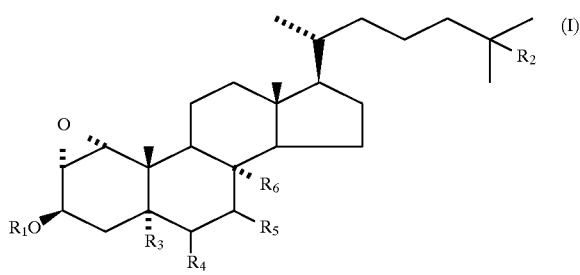

wherein $R_1$ represents a hydrogen atom or a protective group, $R_2$ represents a hydrogen atom or a hydroxyl group, $R_3$, $R_4$, $R_5$ and $R_6$ are such that each of $R_3$ and $R_4$, and $R_5$ and $R_6$ forms a double bond, or $R_4$ and $R_5$ form a double bond, and $R_3$ and $R_6$ bond to dienophile which is capable of protecting a conjugated double bond, with an alcohol, wherein the reaction is carried out in the presence of a base consisting of a metal alkoxide.

2. The process according to claim 1 wherein the epoxy compound is reacted with the alcohol in the presence of a solvent.

3. The process according to claim 2 wherein the solvent is selected from the group consisting of tetrahydrofuran, dioxane, benzene and toluene.

4. The process according to claim 3 wherein the solvent is benzene.

5. The process according to claim 1 wherein the dienophile which is capable of protecting a double bond is a compound of the formula:

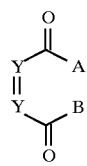

wherein A and B, which may be the same or different, each represents an alkoxy group having from 1 to 4 carbon atoms, or A and B, when taken together, represent a phenylimino group or an o-phenylene group, and Y represents a nitrogen atom of a methine group.

6. The process according to claim 1 wherein the compound of Formula (II) is 2β-(3-hydroxypropoxy)-1α,3β,25-trihydroxycholesta-5,7-diene.

7. The process according to claim 1 wherein the compound of Formula (II) is 2β-(3-hydroxypropoxy)-1α,3β-dihydroxy-5,7-cholestadiene.

8. The process according to claim 1 wherein the compound of Formula (II) is 2β-butoxy-1α,3β, dihydroxycholesta 5,7-diene.

9. The process according to claim 1 wherein the compound of Formula (II) is 2β-cyclohexyloxy-1α,3β, dihydroxycholesta 5,7-diene.

10. The process according to claim 1 wherein the compound of Formula (II) is 2β-cyclohexyloxy-1α,3β,25-trihydroxycholesta 5,7-diene.

11. The process according to claim 1 wherein the compound of Formula (II) is 2β-(4-hydroxybutoxy)-1α,3β,25-trihydroxycholesta 5,7-diene.

12. The process according to claim 1 wherein the compound of Formula (II) is 2β-butoxy-1α,3β,25-trihydroxycholesta 5,7-diene.

13. The process according to claim 1 wherein the compound of Formula (II) is 2β-(5-hydroxypentoxy)-1α,3β,25-trihydroxycholesta 5,7-diene.

14. A process for producing a compound represented by the formula (II):

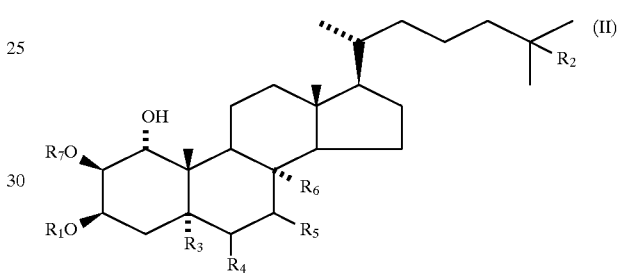

wherein $R_1$ represents a hydrogen atom or a protective group, $R_2$ represents a hydrogen atom or a hydroxyl group, $R_3$, $R_4$, $R_5$ and $R_6$ are such that each of $R_3$ and $R_4$, and $R_5$ and $R_6$ forms a double bond, or $R_4$ and $R_5$ form a double bond, and $R_3$ and $R_6$ bond to dienophile which is capable of protecting a conjugated double bond, and $R_7$ represents a lower alkyl group, a cycloalkyl group or a lower hydroxyalkyl group wherein the hydroxyl group may be protected, which comprises reacting an epoxy compound represented by the formula (I):

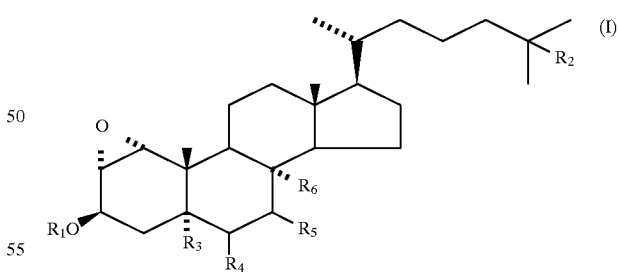

wherein $R_1$ represents a hydrogen atom or a protective group, $R_2$ represents a hydrogen atom or a hydroxyl group, $R_3$, $R_4$, $R_5$, and $R_6$ are such that each of $R_3$ and $R_4$, and $R_5$ and $R_6$ forms a double bond, or $R_4$ and $R_5$ form a double bond, and $R_3$ and $R_6$ bond to dienophile which is capable of protecting a conjugated double bond, with an alcohol, wherein the reaction is carried out under basic conditions and in the presence of a crown ether.

15. A process for producing a compound selected from the group consisting of 2β-(3-hydroxypropoxy)-1α,3β-25-trihydroxycholesta-5,7-diene, 2β-(3-hydroxypropoxy)-1α, 3β-dihydroxy-5,7-cholestadiene, 2β-cyclohexyloxy-1α,3β, dihydroxycholesta 5,7-diene, 2β-cyclohexyloxy-1α,3β,25-trihydroxycholesta 5,7-diene, 2β-(4-hydroxybutoxy)-1α,3β, 25-trihydroxycholesta 5,7-diene, and 2β-(5-hydroxypentoxy)-1α,3β,25-trihydroxycholesta 5,7-diene, which comprises reacting an epoxy compound represented by the formula (I):

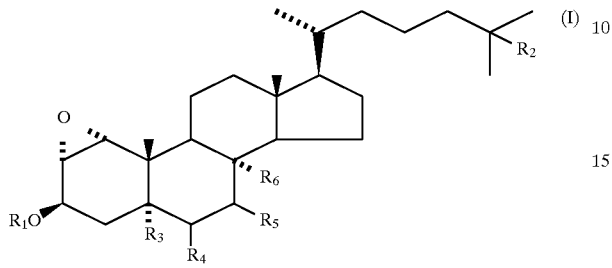

wherein $R_1$ represents a hydrogen atom or a protective group, $R_2$ represents a hydrogen atom or a hydroxyl group, $R_3$, $R_4$, $R_5$ and $R_6$ are such that each of $R_3$ and $R_4$, and $R_5$ and $R_6$ forms a double bond, or $R_4$ and $R_5$ form a double bond, and $R_3$ and $R_6$ bond to dienophile which is capable of protecting a conjugated double bond, with an alcohol, wherein the reaction is carried out under basic conditions.

16. The process according to claim 1 wherein the epoxy compound is reacted with an alcohol in the absence of a solvent, or in the presence of an aromatic solvent.

17. In a process for introducing a substituent into the 2β-position of a steroid derivative by producing a compound represented by the formula (II):

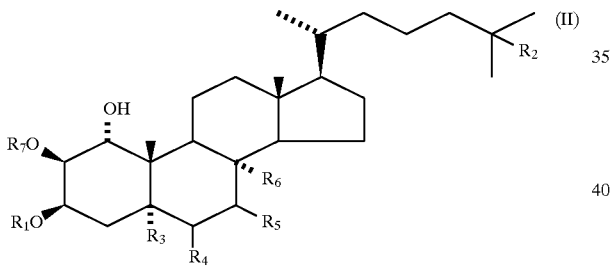

wherein $R_1$ represents a hydrogen atom or a protective group, $R_2$ represents a hydrogen atom or a hydroxyl group, $R_3$, $R_4$, $R_5$ and $R_6$ are such that each of $R_3$ and $R_4$, and $R_5$ and $R_6$, forms a double bond, or $R_4$ and $R_5$ form a double bond, and $R_5$ and $R_6$ bond to a dienophile which is capable of protecting a conjugated double bond, and $R_7$ represents a lower alkyl group, a cycloalkyl group, or a lower hydroxyalkyl group wherein the hydroxyl group may be protected, wherein an epoxy compound represented by formula (I):

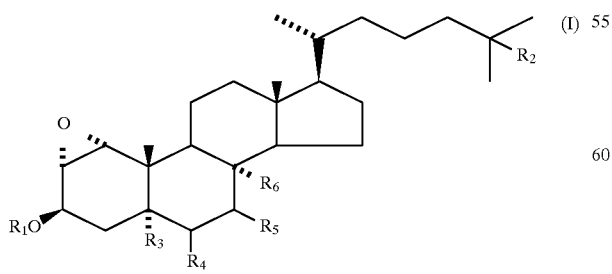

wherein $R_1$ represents a hydrogen atom or a protective group, $R_2$ represents a hydrogen atom or a hydroxyl group, $R_3$, $R_4$, $R_5$ and $R_6$ are such that each of $R_3$ and $R_4$, and $R_5$ and $R_6$, forms a double bond, or $R_4$ and $R_5$ form a double bond, and $R_5$ and $R_6$ bond to a dienophile which is capable of protecting a conjugated double bond, is reacted with an alcohol, the improvement comprising carrying out the reaction under basic conditions and in the presence of a crown ether.

18. In a process for introducing a substituent into the 2β-position of a steroid derivative by producing a compound represented by the formula (II):

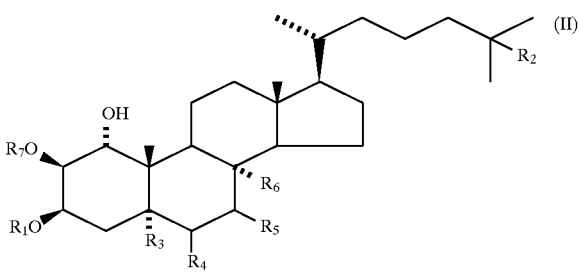

wherein $R_1$ represents a hydrogen atom or a protective group, $R_2$ represents a hydrogen atom or a hydroxyl group, $R_3$, $R_4$, $R_5$ and $R_6$ are such that each of $R_3$ and $R_4$, and $R_5$ and $R_6$, forms a double bond, or $R_4$ and $R_5$ form a double bond, and $R_5$ and $R_6$ bond to a dienophile which is capable of protecting a conjugated double bond, and $R_7$ represents a lower alkyl group, a cycloalkyl group, or a lower hydroxyalkyl group wherein the hydroxyl group may be protected, by reacting an epoxy compound represented by formula (I) with an alcohol,

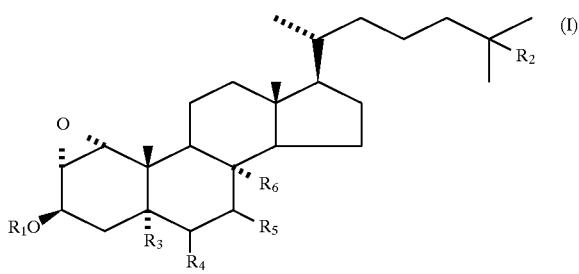

wherein $R_1$ represents a hydrogen atom or a protective group, $R_2$ represents a hydrogen atom or a hydroxyl group, $R_3$, $R_4$, $R_5$ and $R_6$ are such that each of $R_3$ and $R_4$, and $R_5$ and $R_6$, forms a double bond, or $R_4$ and $R_5$ form a double bond, and $R_5$ and $R_6$ bond to a dienophile which is capable of protecting a conjugated double bond, with an alcohol, the improvement comprising conducting said reaction in the presence of a base consisting of a metal alkoxide.

19. The process according to claim 18 wherein the epoxy compound is reacted with an alcohol in the absence of a solvent, or in the presence of an aromatic solvent.

* * * * *